US011142537B2

United States Patent
Yuasa et al.

(10) Patent No.: US 11,142,537 B2
(45) Date of Patent: Oct. 12, 2021

(54) PHOSPHOLIPID CONCENTRATE MANUFACTURING METHOD

(71) Applicant: MARUDAI FOOD CO., LTD., Osaka (JP)

(72) Inventors: Kouki Yuasa, Osaka (JP); Jun Kawamura, Osaka (JP); Satoshi Kotoura, Osaka (JP)

(73) Assignee: MARUDAI FOOD CO., LTD., Osaka (JP)

( * ) Notice: Subject to any disclaimer, the term of this patent is extended or adjusted under 35 U.S.C. 154(b) by 0 days.

(21) Appl. No.: 16/970,167

(22) PCT Filed: Feb. 20, 2019

(86) PCT No.: PCT/JP2019/006418
§ 371 (c)(1),
(2) Date: Aug. 14, 2020

(87) PCT Pub. No.: WO2019/163855
PCT Pub. Date: Aug. 29, 2019

(65) Prior Publication Data
US 2021/0101919 A1    Apr. 8, 2021

(30) Foreign Application Priority Data
Feb. 21, 2018    (JP) .............................. JP2018-028951

(51) Int. Cl.
*C07F 9/10*        (2006.01)
*C11B 1/10*        (2006.01)
(Continued)

(52) U.S. Cl.
CPC ............... *C07F 9/103* (2013.01); *C11B 1/10* (2013.01); *C11B 3/006* (2013.01); *C11B 11/00* (2013.01)

(58) Field of Classification Search
CPC ............. C07F 9/103; C11B 1/10; C11B 3/006
See application file for complete search history.

(56) References Cited

U.S. PATENT DOCUMENTS 8,822,437 B2    9/2014 Ifuku et al.
2012/0283223 A1    11/2012 Ifuku et al.

FOREIGN PATENT DOCUMENTS

JP    H11-018688 A    1/1999
JP    2006-232967 A    9/2006
(Continued)

OTHER PUBLICATIONS

May 21, 2020, Japanese Office Action issued for corresponding JP Application No. 2018-028951.
(Continued)

*Primary Examiner* — Yate' K Cutliff
(74) *Attorney, Agent, or Firm* — Paratus Law Group, PLLC

(57) ABSTRACT

This invention provides a technique that is capable of suppressing variation in the amount of phospholipids obtained in each operation when a phospholipid concentrate is obtained by subjecting an ethanol extract concentrate of livestock or poultry tissue to a degumming step and collecting gum. More specifically, the invention provides a method for producing a phospholipid concentrate from livestock or poultry tissue, comprising step (A) of mixing an ethanol extract concentrate of livestock or poultry tissue with water, the water being in an amount of less than 7 parts by mass per 100 parts by mass of the concentrate, and step (B) of centrifuging the obtained liquid mixture at 2° C. or lower.

12 Claims, 2 Drawing Sheets

Separation into three layers

Separation into two layers

(51) Int. Cl.
  *C11B 3/00*      (2006.01)
  *C11B 11/00*     (2006.01)

(56) References Cited

FOREIGN PATENT DOCUMENTS

| | | | |
|---|---|---|---|
| JP | 2010-063406 A | 3/2010 | |
| JP | 2010-065167 A | 3/2010 | |
| JP | 2016-210696 | * 12/2016 | ........... A61K 31/683 |
| JP | 2016-210696 A | 12/2016 | |
| JP | 2017-200466 A | 11/2017 | |
| WO | WO 2008/146942 A1 | 12/2008 | |
| WO | WO 2010/131718 A1 | 11/2010 | |
| WO | WO 2011/083827 A1 | 7/2011 | |
| WO | WO 2017/191838 A1 | 11/2017 | |

OTHER PUBLICATIONS

Satoshi Kotoura et al., Effects of Dietary Plasmalogens on Brain Function in the Healthy Subjects, Japanese Pharmacology and Therapeutics, 2017, pp. 1511-1521, vol. 45, No. 9.

* cited by examiner

Fig. 2
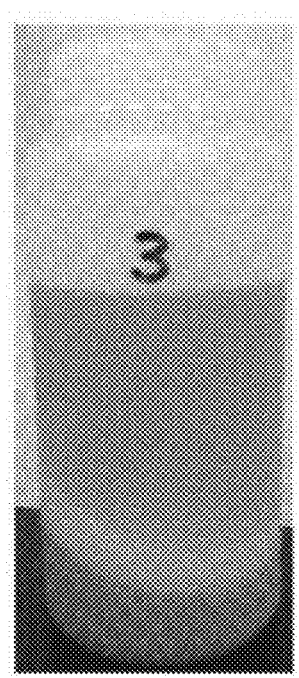 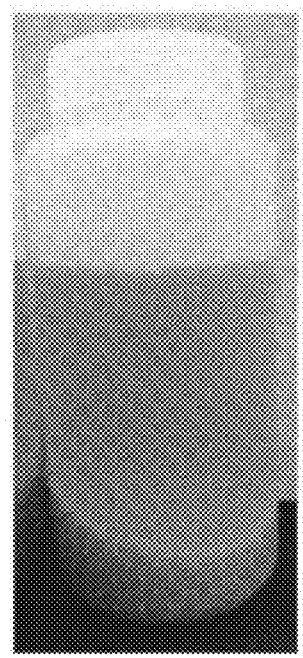
Separation into three layers        Separation into two layers

PHOSPHOLIPID CONCENTRATE MANUFACTURING METHOD

CROSS REFERENCE TO PRIOR APPLICATION

This application is a National Stage Entry of PCT International Patent Application No. PCT/JP2019/006418 (filed on Feb. 20, 2019) under 35 U.S.C. § 371, which claims priority to Japanese Patent Application No. 2018-028951 (filed on Feb. 21, 2018), the contents of each of which are hereby incorporated by reference in their entirety.

TECHNICAL FIELD

The present invention relates to a method for manufacturing a phospholipid concentrate etc.

BACKGROUND ART

Phospholipids are important as constituents of living organisms. In particular, for example, plasmalogens are attracting attention as a functional material that has various effects such as enhancement of memory ability. For this reason, a method for efficiently preparing a phospholipid has been desired.

For example, methods for extracting components such as phospholipids from bird breast meat by ethanol extraction have previously been developed.

CITATION LIST

Patent Literature

PTL 1: JP2006-232967A
PTL 2: JP2010-63406A
PTL 3: JP2010-65167A
PTL 4: JP2016-210696A

SUMMARY OF INVENTION

Technical Problem

The present inventors attempted to extract useful components from livestock or poultry tissue with ethanol to concentrate phospholipids, i.e., types of components considered to be particularly important. In refining oil, it is usual practice to subject extracts from animals and plants to a degumming step and remove gum containing phospholipids as a main component. Considering that phospholipids are components mainly contained in gum as stated above, analysis was performed to efficiently concentrate phospholipids by concentrating ethanol extracts of livestock or poultry tissue, subjecting them to a degumming step, and collecting gum.

This technique enabled the concentration of phospholipids. As the study advanced, however, it was clarified that the amount of phospholipids obtained fluctuated each time concentration was performed. In supplying phospholipid concentrates to the market, equalizing quality is important. Thus, development of a method in which the quality (in particular, the amount of phospholipids) does not vary each time concentration is performed has become necessary.

An object of the present invention is to provide a technique that is capable of suppressing variation in the amount of phospholipids obtained at each operation when a phospholipid concentrate is obtained by subjecting an ethanol extract concentrate of livestock or poultry tissue to a degumming step and collecting gum.

Solution to Problem

The present inventors found treatment principles and conditions for collecting gum in the degumming step, and then made further improvements to accomplish the present invention. As stated above, since the purpose of the present invention is to concentrate phospholipids, gum is collected in the degumming step. It is therefore thought that the degumming step should instead be referred to as a "gum-collecting step." Therefore, below in the present specification, the degumming step is referred to as "the gum-collecting step."

The invention encompasses, for example, the subject matter shown in the following items.

Item 1. A method for producing a phospholipid concentrate from livestock or poultry tissue, or a method for concentrating phospholipids contained in livestock or poultry tissue, the method comprising:
step (A) of mixing an ethanol extract concentrate of livestock or poultry tissue with water, the water being in an amount of less than 7 parts by mass per 100 parts by mass of the concentrate; and
step (B) of centrifuging the obtained liquid mixture at 2° C. or lower.

Item 2. The method according to Item 1, wherein the ethanol extract, concentrate of livestock or poultry tissue has a water content of 1 mass % or less.

Item 3. A method for producing a phospholipid concentrate from livestock or poultry tissue, or a method for concentrating phospholipids contained in livestock or poultry tissue, the method comprising:
step (a1) of concentrating an ethanol extract of livestock or poultry tissue;
step (a2) of mixing the obtained concentrate with water, the water being in an amount of less than 7 parts by mass per 100 parts by mass of the concentrate; and
step (B) of centrifuging the obtained liquid mixture at 2° C. or lower.

Item 4. The method according to Item 3, wherein the ethanol extract of livestock or poultry tissue is concentrated until the water content of the obtained concentrated liquid is 1 mass % or less.

Item 5. The method according to Item 3 or 4, further comprising step (a0) of extracting livestock or poultry tissue with ethanol,
wherein, in this step, when a deposit is formed, heating is first performed to dissolve the deposit, or this step is performed at a temperature at which no deposit is formed.

Item 6. The method according to any one of items 1 to 5, further comprising step (C) of collecting a precipitate formed by the centrifugation.

Item 7. A method for concentrating phospholipids contained in livestock or poultry tissue, comprising:
step (A) of mixing a concentrate of an ethanol extract of livestock or poultry tissue with water, the water being in an amount of less than 7 parts by mass per 100 parts by mass of the concentrate; and
step (B) of centrifuging the obtained liquid mixture at 2° C. or lower.

Item 8. The method according to any one of Items 1 to 7, wherein the livestock or poultry tissue is tissue of birds.

Advantageous Effects of Invention

The method of the present invention is capable of suppressing variation in the amount of phospholipids obtained at each concentration when a phospholipid concentrate is obtained by subjecting an ethanol extract concentrate of livestock or poultry tissue to a degumming step and collecting gum.

BRIEF DESCRIPTION OF DRAWINGS

FIG. 2 shows the results of study on whether the state of the obtained precipitate changes when the centrifugation conditions are changed in the gum-collecting step.

DESCRIPTION OF EMBODIMENTS

Figure 1:
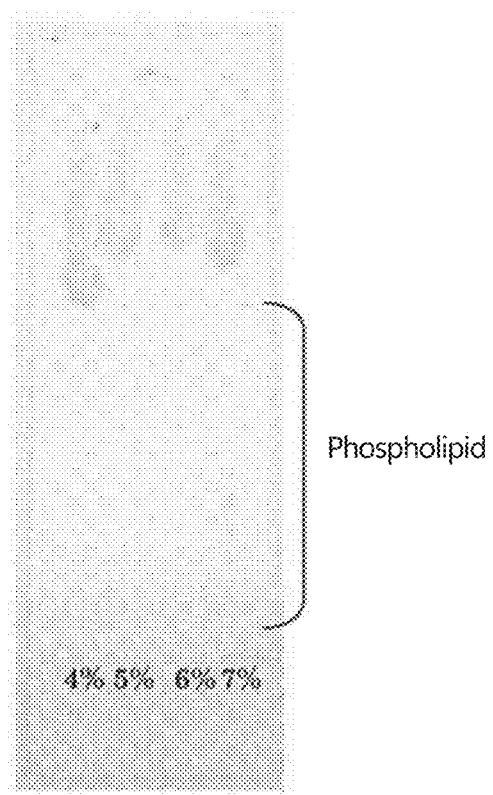
FIG. 1 shows the results of TLC analysis on whether the presence or absence of the amount of phospholipids in the obtained upper layer changes according to the amount of water added to an ethanol extract concentrate in the gum-collecting step.

Below, each embodiment of the present invention is described in more detail.

The method for producing a phospholipid concentrate from livestock or poultry tissue, which is encompassed by the present invention (hereinafter sometimes referred to as "the method for producing a phospholipid concentrate of the present invention") comprises step of mixing an ethanol extract concentrate of livestock or poultry tissue with water, the water being in an amount of less than 7 parts by mass per 100 parts by mass of the concentrate, and step (B) of centrifuging the obtained liquid mixture at 2° C. or lower.

Examples of livestock or poultry include cows, pigs, horses, sheep, goats, birds, and the like. The tissues of mammals containing phospholipids are mainly of, for example, skin, brain, intestines, heart, reproductive organs, meat (in particular, muscle), and the like. Phospholipids can be extracted from these tissues. Examples of birds include chicken, domestic duck, Japanese quail, duck, green pheasant, turkey, and the like. Chickens are particularly preferable in consideration of availability, cost, palatability, etc. The bird tissue is not particularly limited, and is preferably of, for example, bird meat (in particular, bird breast meat), bird skin, internal bird organs, and the like. It is also possible to combine two or more different tissues of one or more different living organisms. The livestock or poultry tissue is more preferably of, for example, bird breast meat, and particularly preferably of chicken breast meat.

The livestock or poultry tissue may be cut into an appropriate size. The tissue may also be dried (in particular, freeze-dried).

The method of ethanol extraction for livestock or poultry tissue is not particularly limited, and a known method or a method that is easily conceivable from the known method can be used. For example, the extraction can be performed by adding ethanol in an amount of about 1 to 5 times that of livestock or poultry tissue, based on mass, followed by stirring or standing. The stirring or standing may be performed with heating. The heating may be performed, for example, at about 30 to 50° C. or about 35 to 45° C. Further, the stirring time or standing time is not particularly limited, and may be, for example, about 0.5 to 24 hours or about 1 to 12 hours. The obtained extract may be subjected to solid-liquid separation by filtration or the like, if necessary. Further, the extraction residue may be subjected to the same operation to obtain an extract again, which may be added to the extract obtained beforehand.

When the temperature is low (in particular, in winter), a deposit may be formed during the extraction process. The temperature at which a deposit is formed is not limited, and is specifically, for example, 10° C.' or lower, 9° C. or lower, 8° C. or lower, 7° C. or lower, 6° C. or lower, 5° C. or lower, 4° C. or lower, 3° C. or lower, 2° C. or lower, 1° C. or lower, or 0° C. or lower. The deposit contains phospholipids; thus, if ethanol extraction is continued while the deposit is left as is, the phospholipids contained in the deposit will not be incorporated into the ethanol extracts. For this reason, the amount of phospholipids contained in the finally obtained phospholipid concentrate may vary. Therefore, when a deposit is formed, it is preferable to first perform heating to dissolve the deposit, or perform the step at a temperature at which no deposit is formed. When heating is performed to dissolve the deposit, the heating temperature is not particularly limited as long as the deposit dissolves and as long as it does not affect the quality. For example, the temperature is about 20 to 30° C. When the ethanol extraction step is performed at a temperature at which no deposit is formed, the step can be performed at a temperature of, for example, about 20 to 30° C.

The method of concentrating the obtained ethanol extract is not particularly limited, and a known method, or a method that is easily conceivable from the known method, can be used. Examples include vacuum concentration, heat concentration, and the like.

The concentration is preferably performed until the water content of the obtained ethanol extract concentrate is 1 mass % or less, more preferably 0.9 mass % or less, 0.8 mass % or less, 0.7 mass % or less, 0.6 mass % or less, or 0.5 mass % or less, and still more preferably 0.4 mass % or less, 0.3 mass % or less, or 0.2 mass % or less. The water content is a value determined by the Kari Fischer method.

The ethanol content of the obtained ethanol extract concentrate is preferably 15 mass % or less, and more preferably 14 mass % or less, 13 mass % or less, 12 mass % or less, 11 mass % or less, 10 mass % or less, 9 mass % or less, or 8 mass % or less. The ethanol content is a value obtained by subtracting the water content from the loss on drying determined by a dry-heat drying method (105° C., 3 hours). For example, when the loss on drying determined by dry heating is 90 mass %, and the water content is 1 mass %, the ethanol content is 100−90−1=9 (mass %).

The amount of water mixed with the ethanol extract concentrate is less than 7 parts by mass per 100 parts by mass of the concentrate. The amount is preferably 6.9 parts by mass or less, 6.8 parts by mass or less, 6.7 parts by mass or less, 6.6 parts by mass or less, 6.5 parts by mass or less, 6.4 parts by mass or less, 6.3 parts by mass or less, 6.2 parts by mass or less, 6.1 parts by mass or less, or 6 parts by mass or less. The lower limit of the amount of water to be mixed is not particularly limited as long as the effects of the present invention are not impaired. For example, the lower limit, is preferably 0.5 parts by mass or more, more preferably 1 part by mass or more, and still more preferably 1.5 parts by mass or more, per 100 parts by mass of the concentrate.

The liquid mixture comprising the ethanol extract concentrate and water is centrifuged, and the resulting precipitate (lower layer) is collected. At this time, centrifugation is performed at a temperature of 2° C. or lower. The temperature is preferably 1° C. or lower, and more preferably 0.5° C. or lower. Further, the temperature adjustment during centrifugation is not particularly limited as long as the concentrate does not freeze and centrifugation can be performed, and may be, for example, −2° C. or higher, −1.5° C. or higher, −1° C. or higher, or −0.5° C. or higher.

The precipitation (lower layer) can be collected, for example, by removing the liquid portion (upper layer). The removal can be performed by a known method, such as decanting. However, the removal is preferably performed by suction.

The collected precipitate can be used as it is as a phospholipid concentrate. It is also possible to use the collected precipitate after it has been dissolved by heating (e.g., about 35 to 45° C.) and stirring. The stirring here is preferably performed in a nitrogen stream.

The present invention also encompasses a method for concentrating phospholipids contained in livestock or poultry tissue. This method comprises step (A) of mixing a concentrate of an ethanol extract of livestock or poultry tissue with water, the water being in an amount of less than 7 parts by mass per 100 parts by mass of the concentrate, and step (B) of centrifuging the obtained liquid mixture at 2° C. or lower. In this method, the same steps can be performed as in the above method for producing a phospholipid concentrate; thus, the same description as for the method for producing a phospholipid concentrate also applies to this method for concentrating phospholipids.

In the present specification, the term "comprising" and "containing" includes the meanings of "consisting essentially of" and "consisting of."

EXAMPLES

The present invention is described in more detail below. However, the present invention is not limited to the following Examples.

As the chicken breast meat, freeze-dried chicken breast meat (FD chicken breast meat) was used. The expression "%" denotes mass (w/w) unless otherwise specified.

Ethanol Extraction

FD chicken breast meat (42 kg) was placed in an extraction tank. Then, 99% ethanol in an amount 4 times (w/v; 168 L) that of the FD chicken breast meat was placed in the extraction tank. After the tank was purged with nitrogen, the mixture was heated with stirring, and when the temperature reached 40° C., the mixture was allowed to stand for 90 minutes. After filtration through a 30-mesh filter, the extract was collected in a drum. The first extraction residue was placed in the extraction tank, and 99% ethanol in an amount 2.5 times (w/v; 105 L) that of the ED chicken breast meat was placed in the extraction tank. After the tank was purged with nitrogen, the mixture was heated with stirring, and when the temperature reached 40° C., the mixture was allowed to stand for 90 minutes. After filtration through a 30-mesh filter, the extract was collected in a drum. The extract was suction-filtered with 10S filter paper. The obtained liquid was used as an ethanol extract.

Concentration of Ethanol Extract Under Reduced Pressure

The ethanol extract was concentrated under reduced pressure at an internal temperature of 40° C. or lower to about the volume that could be entirely contained in a 50-L vat (about 8 kg). The resulting primary concentrated liquid was placed in a 50-L vat, and the pressure was reduced at an external temperature of 50 to 60° C. After the obtained concentrated liquid was filtered through a 30-mesh filter, the weight was measured. The weight was 5.12 kg. This concentrated liquid for use as an ethanol extract concentrate was stored at 4° C. until use.

The loss on drying of the ethanol extract concentrate was determined by a dry-heat drying method (105° C., 3 hours), while the water content was determined by the Karl Fischer method. The ethanol concentration was calculated by the subtraction method. As a result, the loss on drying was 8.05%, the water content was 0.15%, and the ethanol was 7.9%.

Collecting Gum

Study on Amount of Mixed Water

The ethanol extract concentrate was mixed with heating to 20° C., and 5 g each was weighed. To the concentrates, water in a mass ratio of 4, 5, 6, or 7% was added (i.e., 0.2 g, 0.25 g, 0.3 g, or 0.35 g). After the mixture was sufficiently stirred for 5 minutes, centrifugation was performed at 2000×g at 4° C. for 15 minutes to separate the mixture into two layers. The hardness of the precipitate and the phospholipids (PL) contained in the upper layer were confirmed by thin-layer chromatography (TLC). FIG. 1 and Table 1 show the TLC results.

TABLE 1

| Amount of water | 4% | 5% | 6% | 7% |
|---|---|---|---|---|
| State of precipitate | Soft | Slightly hard | Harder than 5% over time | Hard |
| State of upper layer (TLC results) | No PL in the upper layer | No PL in the upper layer | No PL in the upper layer | PL is present in the upper layer |

The results revealed that the hardness of the precipitate and the presence or absence of PL in the upper layer greatly varied according to a slight difference in the amount of water mixed. A further study was conducted by selecting a mixed water amount of 6%, at which separation of the precipitate (lower layer) from the liquid (upper layer) would be easily performed, and the highest efficiency in collecting PL would be achieved.

Study on Centrifugation Conditions

While the ethanol extract concentrate was heated to 20° C., water was mixed, and centrifugation was performed as follows.

(I): Water in a mass ratio of 6% (18 g) was added to 300 g of the concentrate, and the mixture was stirred for 5 minutes with a propeller stirrer and hydrated.

(II): Water in a mass ratio of 6% (18 g) was added to 300 g of the concentrate, and the mixture was shaken 120 times/min for 5 minutes and hydrated.

Separation into two layers was observed under both conditions (I) and (II) when centrifugation was performed at 2000×g at 9° C. for 15 minutes. However, the precipitates immediately after centrifugation were so soft in both cases that solid-liquid separation was difficult. According to TLC analysis, no phospholipids were detected in the upper layer. Therefore, further study was conducted to find the conditions under which a harder precipitate was formed to an extent that at least solid-liquid separation could be easily performed.

(III): Water in a mass ratio of 6% (18 g) was added to 300 g of the concentrated liquid, and the mixture was shaken 120 times/min for 5 minutes and hydrated; thereafter, the resulting product was allowed to stand at 4° C. overnight. When centrifugation was performed at 2000×g at 4° C. for 15 minutes, separation into three layers was observed. (FIG. 2, left side). The middle and lower layers were solid, and solid-liquid separation was possible. However, it was difficult to separate the middle layer containing neutral lipids from, the lower layer containing phospholipids.

(IV): Water in a mass ratio of 6% (18 g) was added to 300 g of the concentrated liquid, and the mixture was shaken 120 times/minute for 5 minutes and hydrated. When centrifugation was performed at 2000×g at 0° C. for 15 minutes, separation into two layers was observed (FIG. 2, right side). The precipitate immediately after the centrifugation was hard, and solid-liquid separation was possible.

The above results revealed that it is important to perform centrifugation at a temperature lower than 4° C.

Under condition (IV), the collected precipitate (lower layer) easily dissolved by stirring at 40° C. for 5 minutes in a nitrogen stream. The amount of the liquid dissolved was 113.5 g; thus the yield, was 37.8%. Further, the dissolved precipitate was analyzed by thin-layer chromatography (TLC). The results confirmed that a large amount of phospholipids was contained.

The above results revealed that preparation of a phospholipid concentrate from an ethanol extract under the condition (IV) can reduce the risk of loss of phospholipids during the operation, thus suppressing variation in the amount of phospholipids obtained at each operation.

Difference Between Seasons

As described above, the amounts of obtained phospholipids varied less at each operation under condition (IV). However, when winter came, the amount of obtained phospholipids decreased compared to the amount obtained until then. Therefore, further study was conducted. It was then clarified that at a low temperature, deposition would occur when the filtration operation in preparing an ethanol extract took a long period of time, or when the product was allowed to stand for a long period of time before the filtration operation. TLC analysis confirmed that the deposit contained phospholipids. It was thought that when deposition occurred, the deposit would be removed by filtration, and as a result, the amount of phospholipids would decrease.

Therefore, in particular, in winter, when a deposit was formed at the time when ethanol extraction was performed, it was determined to continue the operation after heating and melting were performed. Alternatively, it was determined to perform the ethanol extraction operation itself at a temperature at which no deposit would be formed (e.g., about 25° C.).

The invention claimed is:

1. A method for producing a phospholipid concentrate from livestock or poultry tissue, the method comprising:
    step (A) of mixing an ethanol extract concentrate of livestock or poultry tissue with water, the water being in an amount of 0.5 parts by mass to less than 7 parts by mass per 100 parts by mass of the concentrate, thereby obtaining a mixture; and
    step (B) of centrifuging the mixture at 2° C. or lower.

2. The method according to claim 1, wherein the ethanol extract concentrate of livestock or poultry tissue has a water content of 1 mass % or less.

3. A method for producing a phospholipid concentrate from livestock or poultry tissue, the method comprising:
    step (a1) of concentrating an ethanol extract of livestock or poultry tissue;
    step (a2) of mixing the obtained concentrate with water, the water being in an amount of 0.5 parts by mass to less than 7 parts by mass per 100 parts by mass of the concentrate, thereby obtaining a mixture; and
    step (B) of centrifuging the mixture at 2° C. or lower.

4. The method according to claim 3, wherein the ethanol extract of livestock or poultry tissue is concentrated until the water content of the obtained concentrated liquid is 1 mass % or less.

5. The method according to claim 3, further comprising step (a0) of extracting livestock or poultry tissue with ethanol,
    wherein in the step (a0), when a deposit is formed, heating is performed to dissolve the deposit, or the step (a0) is performed at a temperature at which no deposit is formed.

6. The method according to claim 1, further comprising step (C) of collecting a precipitate formed by the centrifugation.

7. A method for concentrating phospholipids contained in livestock or poultry tissue, comprising:
    step (A) of mixing a concentrate of an ethanol extract of livestock or poultry tissue with water, the water being in an amount of 0.5 parts by mass to less than 7 parts by mass per 100 parts by mass of the concentrate, thereby obtaining a mixture; and
    step (B) of centrifuging the mixture at 2° C. or lower.

8. The method according to claim 1, wherein the livestock or poultry tissue is tissue of birds.

9. The method according to claim 4, further comprising step (a0) of extracting livestock or poultry tissue with ethanol,
    wherein in the step (a0), when a deposit is formed, heating is performed to dissolve the deposit, or the step (a0) is performed at a temperature at which no deposit is formed.

10. The method according to claim 3, further comprising step (C) of collecting a precipitate formed by the centrifugation.

11. The method according to claim 3, wherein the livestock or poultry tissue is tissue of birds.

12. The method according to claim 7, wherein the livestock or poultry tissue is tissue of birds.

* * * * *